US009035058B2

(12) United States Patent
Weston et al.

(10) Patent No.: US 9,035,058 B2
(45) Date of Patent: May 19, 2015

(54) SYNTHESIS OF MSE-FRAMEWORK TYPE MOLECULAR SIEVES

(71) Applicants: Simon C. Weston, Annandale, NJ (US); Karl G. Strohmaier, Port Murray, NJ (US); Hilda B. Vroman, Piscataway, NJ (US)

(72) Inventors: Simon C. Weston, Annandale, NJ (US); Karl G. Strohmaier, Port Murray, NJ (US); Hilda B. Vroman, Piscataway, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 14/541,777

(22) Filed: Nov. 14, 2014

(65) Prior Publication Data
US 2015/0087841 A1 Mar. 26, 2015

Related U.S. Application Data

(62) Division of application No. 13/649,283, filed on Oct. 11, 2012, now Pat. No. 8,916,130.

(51) Int. Cl.
*C07D 453/02* (2006.01)
*C07D 211/12* (2006.01)

(52) U.S. Cl.
CPC ............ *C07D 453/02* (2013.01); *C07D 211/12* (2013.01)

(58) Field of Classification Search
None
See application file for complete search history.

(56) References Cited

U.S. PATENT DOCUMENTS

| | | | |
|---|---|---|---|
| 3,354,078 | A | 11/1967 | Miale et al. |
| 4,391,785 | A | 7/1983 | Rosinski et al. |
| 4,481,177 | A | 11/1984 | Valyocsik |
| 4,508,837 | A | 4/1985 | Zones |
| 4,557,919 | A | 12/1985 | Sumitani et al. |
| 4,689,207 | A | 8/1987 | Zones |
| 5,187,132 | A | 2/1993 | Zones et al. |
| 6,027,707 | A | 2/2000 | Casci et al. |
| 6,049,018 | A | 4/2000 | Calabro et al. |
| 6,086,848 | A | 7/2000 | Nakagawa et al. |
| 6,649,141 | B2 | 11/2003 | Camblor Fernandez et al. |
| 7,198,711 | B1 | 4/2007 | Chester et al. |
| 7,485,766 | B2 | 2/2009 | Burton, Jr. et al. |
| 7,648,694 | B2 | 1/2010 | Burton, Jr. |
| 2008/0035524 | A1 | 2/2008 | Corma Canos et al. |
| 2009/0104112 | A1 | 4/2009 | Burton, Jr. et al. |
| 2009/0214418 | A1 | 8/2009 | Burton, Jr. et al. |
| 2009/0318696 | A1 | 12/2009 | Strohmaier et al. |
| 2010/0081775 | A1 | 4/2010 | Moscoso et al. |
| 2010/0272624 | A1 | 10/2010 | Fecant et al. |

FOREIGN PATENT DOCUMENTS

| | | |
|---|---|---|
| EP | 1194375 B1 | 12/2003 |
| EP | 1852394 A1 | 1/2006 |
| EP | 2174911 A1 | 4/2010 |
| FR | 2936791 A1 | 7/2008 |
| JP | 2004010537 | 1/2004 |
| WO | 2009004131 A1 | 1/2009 |
| WO | 2009090336 A1 | 7/2009 |
| WO | 2010015732 A1 | 2/2010 |
| WO | 2010015733 A1 | 2/2010 |
| WO | 2010015736 A1 | 2/2010 |
| WO | 2010015737 A1 | 2/2010 |
| WO | 2010065318 A2 | 6/2010 |
| WO | 2010065319 A2 | 6/2010 |

OTHER PUBLICATIONS

Lobo et al., "Synthesis and Rietveld Refinement of the Small-Pore Zeolite SSZ-16", Chemistry of Materials, Oct. 15, 1996, pp. 2409-241, vol. 8, iss.10, ACS Publications.
Jackowski et al., "Diquaternary Ammonium Compounds in Zeolite Synthesis: Cryclic and Polycyclic N-Heterocycles Connected by Methylene Chains", Journal of the American Chemical Society, Jan. 7, 2009, pp. 1092-1100, vol. 131, iss. 3, ACS Publications.
Jackowski et al., "A study on zeolite synthesis from diquaternary ammonium compounds; the effect of changing end-group heterocycles in the HF/Sio2 synthesis of molecular sieves", Studies in Surface Science and Catalysis, Zeolites and Related Materials, Sep. 2, 2008, pp. 111-116, vol. 174, Part A, Elsevier, ScienceDirect.
Zones et al., "A Most Unusual Zeolite Templating: Cage to Cage Connection of One Guest Molecule", Journal of Physical Chemistry C, Apr. 21, 2010, pp. 8899-8904, vol. 114, iss.19, ACS Publications.
Zones et al., "Further studies on the conversion of Cubic P zeolite to high silica organozeolites", Zeolites, Sep. 1988, pp. 409-415, vol. 8, iss. 5, Butterworth Publishers.
Liu et al., The First Zeolite with Three-Dimensional Intersecting Straight-Channel System of 12-Membered Rings, Journal of the American Chemical Society, May 11, 2001, pp. 5370-5371, vol. 123, iss. 22, ACS Publications.
Carati et al., "Synthesis of zeolites using N,N'-tetramethylen-bis-(N-methylpiperidinium) dihydroxydes as directing agent", Studies in Surface Science and Catalysis, Zeolites and Related Materials, 2008, pp. 269-272, vol. 174, Part A, Elsevier, ScienceDirect.
Tagliabue et al., "Multivariate approach to zeolite synthesis", Catalysis Today, May 2, 2003, pp. 405-412, vol. 81, iss. 3, Elsevier, ScienceDirect.

(Continued)

*Primary Examiner* — Timothy R Rozof
(74) *Attorney, Agent, or Firm* — David M. Weisberg

(57) ABSTRACT

A method of synthesizing a crystalline molecular sieve having an MSE framework type comprises crystallizing a reaction mixture comprising a source of water, a source of an oxide of a tetravalent element, Y, selected from at least one of silicon, tin, titanium, vanadium, and germanium, optionally a source of a trivalent element, X, a source of an alkali or alkaline earth metal, M, and a source of organic dications, Q, such as 3-hydroxy-1-(4-(1-methylpiperidin-1-ium-1-yl)butyl)quinuclidin-1-ium, 3-hydroxy-1-(5-(1-methylpiperidin-1-ium-1-yl)pentyl)quinuclidin-1-ium, 1,1'-(butane-1,4-diyl)bis(1-methylpiperidin-1-ium), 1,1'-(pentane-1,5-diyl)bis(1-methylpiperidin-1-ium), 1,1'-(hexane-1,6-diyl)bis(1-methylpiperidin-1-ium), and 1,1'-((3as,6as)-octahydropentalene-2,5-diyl)bis(1-methylpiperidin-1-ium).

3 Claims, 1 Drawing Sheet

(56) References Cited

OTHER PUBLICATIONS

Koller et al., "Five-Coordinate Silicon in High-Silica Zeolites", Journal of the American Chemical Society, Mar. 23, 1999, pp. 3368-3376, vol. 121, iss. 14, ACS Publications.
Diaz-Cabanas et al., "Zeolite syntheses using linear diquats of varying length in fluoride media. The synthesis of ITQ-8, ITQ-10, ITQ-14 and high silica Nu-87", Journal of Materials Chemistry, Jan. 4, 2002, pp. 249-257, vol. 12, iss. 2.
Barrett et al., "Synthesis of defect-free pure silica polymorphs of low framework density in aqueous fluoride media", Proceedings of the International Zeolite Conference, 12th, Baltimore, Jul. 5-10, 1998 (1999), Meeting Date 1998, pp. 1495-1502, vol. 3.
Corma et al., "Amorphous microporous molecular sieves with different pore dimensions and topologies: Synthesis, characterization and catalytic activity", Microporous and Mesoporous Materials, Feb. 24, 2006, pp. 39-46, vol. 89, issues 1-3, Elsevier, ScienceDirect.
Springuel-Huet et al., "Amorphous microporous molecular sieves studied by laser-polarized 129Xe NMR spectroscopy", Studies in Surface Science and Catalysis, From Zeolites to Porous MOF Materials, Jan. 2007, pp. 812-817, vol. 170, Part A, Elsevier B.V.
Noble et al., "Microporous magnesium aluminophosphate STA-1: synthesis with a rationally designed template and structure elucidation by microcrystal diffraction", Angewandte Chemie, International Edition in English, Feb. 3, 1997, pp. 81-83, vol. 36, iss. 1/2, Wiley Online Library.
DeMoor et al., "Imaging the assembly process of the organic-mediated synthesis of a zeolite", Chemistry—A European Journal, Jun. 24, 1999, pp. 2083-2088, vol. 5, iss. 7, Wiley-VCH.
Noble et al., "The templated synthesis and structure determination by synchrotron microcrystal diffraction of the novel small pore magnesium aluminophosphate STA-2", Journal of the Chemical Society, Dalton Transactions: Inorganic Chemistry (1997), (23), 4485-4490.
Dorset et al., "Crystal Structure of Zeolite MCM-68: A New Three-Dimensional Framework with Large Pores", Journal of Physical Chemistry B, Jan. 6, 2006, pp. 2045-2050, vol. 110, iss. 5, ACS Publications.
Weisz et al., "Superactive Crystalline Aluminosilicate Hydrocarbon Catalysts", Journal of Catalysis, 4, 527 (1965).
Maile et al, "Catalysis by Crystalline Aluminosilicates IV. Attainable Catalytic Cracking Rate Constants, and Superactivity", Journal of Catalysis, 6, 278 (1966).
Olson et al., "Chemical and Physical Properties of the ZSM-5 Substitutional Series", Journal of Catalysis, Feb. 2, 1980, pp. 390-396, vol. 61 iss. 2, Academic Press.
Parikh et al., "Non-thermal calcination by ultraviolet irradiation in the synthesis of microporous materials", Microporous and Mesoporous Materials, Dec. 1, 2004, pp. 17-22, vol. 76, issues 1-3, Elsevier, ScienceDirect.
Koyama et al., "Multi-Dimensional Microporous Silicate That is Isomorphous to Zeolite MCM-68", Angewandte Chemie International Edition, Jan. 25, 2008, pp. 1042-1046, vol. 47, iss. 6, Wiley Online Library.
Moretti et al., "Zeolite synthesis in the presence of organic components", La Chimica E L'Industria, Jan. 1, 1985, pp. 21-34, vol. 67, iss. 1-2, Societa Chimica Italiano, Milano, IT.
International Search Report and Written Opinion from PCT/US2012/059693 dated Dec. 18, 2012. (Related case).
International Search Report and Written Opinion from PCT/US2012/059678 dated Feb. 7, 2013.

X-ray diffraction pattern of MCM-68 prepared with SDA (VIII)
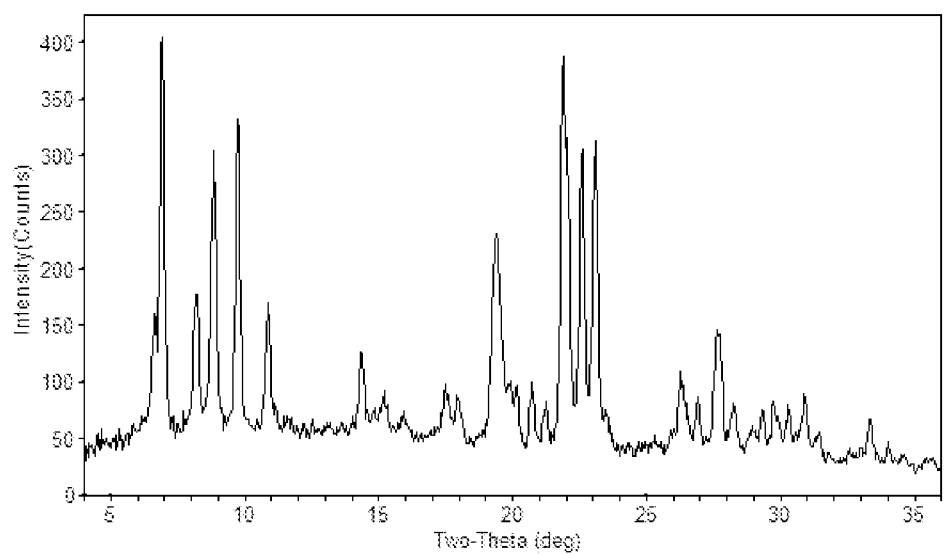

SYNTHESIS OF MSE-FRAMEWORK TYPE MOLECULAR SIEVES

CROSS-REFERENCE TO RELATED APPLICATIONS

This application claims priority to U.S. application Ser. No. 13/649,283, filed on Oct. 11, 2012, and recently allowed, which itself claims the benefit of U.S. Provisional Application No. 61/546,335, filed on Oct. 12, 2011, the entire contents of both of which are hereby incorporated by reference herein.

FIELD OF THE INVENTION

This invention relates to the synthesis of crystalline molecular sieves of the MSE framework-type, such as MCM-68, and to their use in organic conversion processes.

BACKGROUND OF THE INVENTION

MCM-68 is a single crystalline phase molecular sieve material which has a unique 3-dimensional channel structure comprising one 12-membered ring channel system and two 10-membered ring channel systems, in which the channels of each system extend perpendicular to the channels of the other systems and in which the 12-ring channels are generally straight and the 10-ring channels are tortuous (sinusoidal). The framework structure of MCM-68 has been assigned code MSE by the Structure Commission of the International Zeolite Association.

The composition and characterizing X-ray diffraction pattern of MCM-68 are disclosed in U.S. Pat. No. 6,049,018, which also describes the synthesis of the molecular sieve in the presence of a structure directing agent comprising the N,N,N',N'-tetraethylbicyclo[2.2.2]oct-7-ene-2,3:5,6-dipyrrolidinium dication. The entire contents of U.S. Pat. No. 6,049,018 are incorporated herein by reference.

U.S. Pat. No. 6,049,018 exemplifies the use of MCM-68 as a catalyst in aromatic alkylation and transalkylation reactions. In addition, U.S. Pat. No. 7,198,711 discloses that MCM-68 shows activity in the catalytic cracking of hydrocarbon feedstocks to produce an enhanced yield of butylenes and isobutene, with the MCM-68 either being the primary cracking catalyst or an additive component in conjunction with a conventional large pore cracking catalyst, such as zeolite Y.

The commercial development of MCM-68 has been hindered by the high cost of the N,N,N',N'-tetraethylbicyclo[2.2.2]oct-7-ene-2,3:5,6-dipyrrolidinium dication structure directing agent required in U.S. Pat. No. 6,049,018 for its synthesis and hence there has been significant interest in finding alternative, less expensive structure directing agents for the synthesis of MCM-68.

In U.S. Patent Application Publication No. 2009/0318696, it is stated that 1,1-dialkyl-4-cyclohexylpiperazin-1-ium cations and 1,1-dialkyl-4-alkylcyclohexylpiperazin-1-ium cations are effective as structure directing agents in the synthesis of MCM-68. U.S. Patent Application Publication No. 2009/0318696 describes the use of MCM-68 seeds in the synthesis of MCM-68.

According to the present invention, it has now been found that cations described herein are effective as structure directing agents in the synthesis of MCM-68. Furthermore, it has been found that these cations may be produced conveniently and inexpensively from commercially available raw materials. Moreover, it has been found that MCM-68 can be prepared with these cations without the need to be seeded with MCM-68 seeds.

SUMMARY OF THE INVENTION

In one aspect, the present invention resides in a method of synthesizing a crystalline molecular sieve having a structure of the MSE framework type, preferably MCM-68, the method comprising crystallizing a reaction mixture comprising a source of water, a source of an oxide of a tetravalent element, Y, selected from at least one of silicon, tin, titanium, vanadium and germanium, optionally a source of a trivalent element, X, a source of an alkali or alkaline earth metal, M, and a source of organic cations, Q, having the following general structure: $R_1$-$R_3$-$R_2$; where $R_1$ and $R_2$ are the same or different, and where $R_1$ or $R_2$ or both $R_1$ and $R_2$ are an N-alkylpiperidinium group of the formula

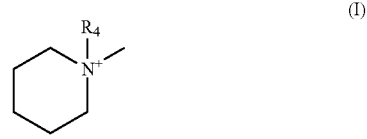

or where $R_1$ or $R_2$ or both $R_1$ and $R_2$ are a quinuclidinium group of the formula

where $R_3$ is an polymethylene group of the formula $(CH_2)_n$, where n is from 4 to 6, or where $R_3$ is a cycloalkylene group having from 5 to 8 carbon atoms, and where $R_4$ is an alkyl group having 1 to 4 carbon atoms.

An example of an organic cation, Q, is a 3-hydroxy-1-(4-(1-methylpiperidin-1-ium-1-yl)butyl)quinuclidin-1-ium dication of the formula

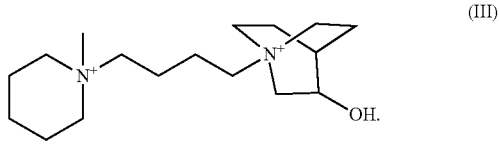 [SMILES: C[N+]1(CCCC[N+]23CCC(CC2)C(O)C3)CCCCC1]

Another example of an organic cation, Q, is a 3-hydroxy-1-(5-(1-methylpiperidin-1-ium-1-yl)pentyl)quinuclidin-1-ium dication of the formula

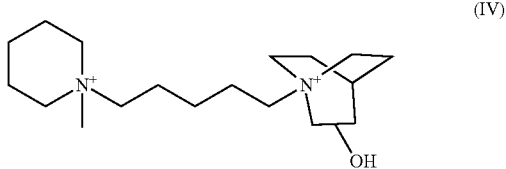

Another example of an organic cation, Q, is a 1,1'-(butane-1,4-diyl)bis(1-methylpiperidin-1-ium)dication of the formula

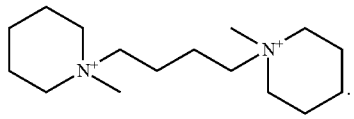

(V)

Another example of an organic cation, Q, is a 1,1'-(pentane-1,5-diyl)bis(1-methylpiperidin-1-ium)dication of the formula

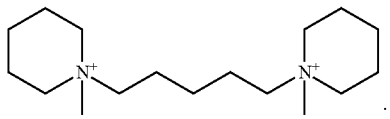

(VI)

Another example of an organic cation, Q, is a 1,1'-(hexane-1,6-diyl)bis(1-methylpiperidin-1-ium)dication of the formula

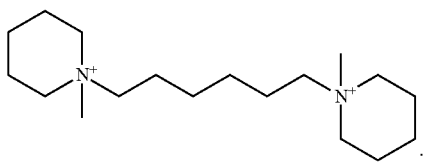

(VII)

Another example of an organic cation, Q, is a 1,1'-((3as,6as)-octahydropentalene-2,5-diyl)bis(1-methylpiperidin-1-ium)dication of the formula

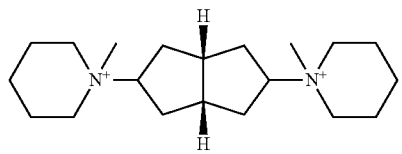

(VIII)

The source of the organic dication may be any salt not detrimental to the formation of the crystalline material of the invention, for example, the halide or hydroxide salt.

The molar ratio $Q/YO_2$ in the reaction mixture may be in the range of from about 0.01 to about 1.0, such as from about 0.05 to about 0.7.

The reaction mixture may comprise a source of an oxide of trivalent element, X, selected from at least one of aluminum, boron, gallium, iron, and chromium, such that, for example, the molar ratio $YO_2/X_2O_3$ in the reaction mixture is in the range of from about 4 to about 200, such as from about 8 to about 120.

In one embodiment, the reaction mixture can have the following molar composition:

| | |
|---|---|
| $YO_2/X_2O_3$ | ~4 to ~200 |
| $H_2O/YO_2$ | ~5 to ~200 |
| $OH^-/YO_2$ | ~0.05 to ~1 |
| $M/YO_2$ | ~0.05 to ~2 |
| $Q/YO_2$ | ~0.01 to ~1. |

In another embodiment, the reaction mixture can have the following molar composition:

| | |
|---|---|
| $YO_2/X_2O_3$ | ~8 to ~120 |
| $H_2O/YO_2$ | ~14 to ~50 |
| $OH^-/YO_2$ | ~0.10 to ~0.53 |
| $M/YO_2$ | ~0.15 to ~0.9 |
| $Q/YO_2$ | ~0.05 to ~0.7. |

In a particular embodiment, the tetravalent element, Y, comprises or is silicon, the trivalent element, X, comprises or is aluminum, and said alkali or alkaline earth metal, M, is sodium and/or potassium.

The reaction mixture may optionally comprise seeds of MSE framework type molecular sieve, for example, such that the molar ratio of seeds/$YO_2$ in said reaction mixture is between about 0.001 and about 0.1. However, such seeds need not be included in the reaction mixture in order to make MCM-68.

Crystallizing may be conducted at a temperature between about 100° C. and about 200° C. for up to about 28 days, such as at a temperature between about 145° C. and about 175° C. for about 24 hours to about 170 hours.

As synthesized forms of a crystalline molecular sieve having the MSE framework type produced by embodiments described herein may contain within its pore structure cations, Q, as defined above.

Zeolites produced by methods describe herein may be used in an organic conversion process comprising contacting an organic feed with a catalyst comprising a calcined form of the crystalline MSE framework type molecular sieve described herein.

Aspects of the present invention can involve new compositions of matter. For example, there is provided a dication of the structure $R_1$-$R_3$-$R_2$, where $R_1$ is an N-alkylpiperidinium group of the formula

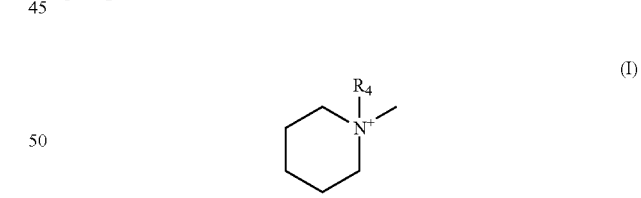

(I)

where $R_2$ is a quinuclidinium group of the formula

(II)

where $R_3$ is an polymethylene group of the formula $(CH_2)_n$, where n is from 4 to 6, and where $R_4$ is an alkyl group having 1 to 4 carbon atoms. Examples of these dications include a 3-hydroxy-1-(4-(1-methylpiperidin-1-ium-1-yl)butyl)quinuclidin-1-ium dication of Formula (III) and a 3-hydroxy-1-(5-(1-methylpiperidin-1-ium-1-yl)pentyl)quinuclidin-1-ium dication of Formula (IV).

Another compound provided according to aspects of the present invention is a 1,1'-((3as,6as)-octahydropentalene-2,5-diyl)bis(1-methylpiperidin-1-ium)dication of Formula (VIII).

BRIEF DESCRIPTION OF THE DRAWING

FIG. 1 is an X-ray diffraction pattern of MCM-68 produced using 1,1'-((3as,6as)-octahydropentalene-2,5-diyl)bis(1-methylpiperidin-1-ium)dications as the structure directing agent according to the process of Example 20.

DETAILED DESCRIPTION OF THE EMBODIMENTS

Described herein is a method of synthesizing a crystalline molecular sieve having the MSE framework type, such as MCM-68, using Q cations as a structure directing agent. Also described herein is the use of the calcined form of the resultant MSE framework type crystalline molecular sieve as a catalyst in organic conversion reactions, such as in aromatic alkylation and transalkylation reactions and in the catalytic cracking of hydrocarbon feedstocks.

MCM-68 is a synthetic porous single crystalline phase material that has a unique 3-dimensional channel system comprising one 12-membered ring channel system and two 10-membered ring channel systems, in which the channels of each system extend perpendicular to the channels of the other systems and in which the 12-ring channels are generally straight and the 10-ring channels are generally tortuous (sinusoidal). The framework structure of MCM-68 has been assigned code MSE by the Structure Commission of the International Zeolite Association.

In its calcined form, MCM-68 has an X-ray diffraction (XRD) pattern which is distinguished from the patterns of other known as-synthesized and/or thermally treated crystalline materials by the lines listed in Table 1 below.

TABLE 1

| d(Å) | Relative Intensity [100 × I/I$_o$] |
|---|---|
| 13.60 +/− 0.39 | S |
| 13.00 +/− 0.37 | VS |
| 10.92 +/− 0.31 | M |
| 10.10 +/− 0.29 | M |
| 9.18 +/− 0.26 | VS |
| 8.21 +/− 0.23 | W |
| 4.58 +/− 0.13 | W |
| 4.54 +/− 0.13 | W |
| 4.45 +/− 0.13 | VW-W |
| 4.32 +/− 0.12 | VW |
| 4.22 +/− 0.12 | VW |
| 4.10 +/− 0.12 | VS |
| 4.05 +/− 0.11 | M |
| 3.94 +/− 0.11 | M |
| 3.85 +/− 0.11 | M |
| 3.80 +/− 0.11 | VW |
| 3.40 +/− 0.10 | W |
| 3.24 +/− 0.09 | W |
| 2.90 +/− 0.08 | VW |

Though described as d-spacings herein, the peaks observed in XRD spectra have maxima in intensity, and the peak maxima correspond to the d-spacing "lines" listed herein. These X-ray diffraction data were collected with a Bruker D8 Discover diffraction system using Cu-Kα radiation and equipped with a Göbel mirror and HI-STAR area detector.

The XRD spectra were recorded by measuring the diffraction pattern in two frames, the first frame from about 4° to about 20° 2θ, and the second from about 20° to about 36° 2θ. The two-dimensional diffraction patterns were integrated and converted to 1-dimensional plots of 2θ versus intensity using the Bruker GADDs software. The interplanar (d-) spacings were calculated in Angstrom units, and the relative intensities of the lines, I/I$_o$, adjusted as percentages of the intensity of the strongest line, I$_o$, above background, were derived with the use of Materials Data, Inc., Jade software peak search algorithm. The intensities were uncorrected for Lorentz and polarization effects. The relative intensities are given in terms of the symbols VS=very strong (80-100%), S=strong (60-80%), M=medium (40-60%), W=weak (20-40%), and VW=very weak (0-20%). It should be understood that diffraction data listed for these samples as single lines may consist of multiple overlapping lines which under certain conditions, such as differences in crystallographic changes, may appear as resolved or partially resolved lines. Typically, crystallographic changes can include minor changes in unit cell parameters and/or changes in crystal symmetry, without a corresponding change in the structure. These minor effects, including changes in relative intensities, can additionally or alternately occur as a result of differences in cation content, framework composition, nature and degree of pore filling, crystal size and shape, preferred orientation, and thermal and/or hydrothermal history, inter alia.

The structure of MCM-68 is further discussed in U.S. Pat. No. 7,198,711 and in the *Journal of Physical Chemistry B*, 110, 2045 (2006).

MCM-68 has a chemical composition involving the molar relationship: $X_2O_3$:(n)$YO_2$, wherein X is a trivalent element selected from at least one of aluminum, boron, gallium, iron, and chromium, preferably at least including aluminum; Y is a tetravalent element selected from at least one of silicon, tin, titanium, vanadium, and germanium, preferably at least including silicon; and n is at least about 4, such as from about 4 to about 100,000, and can typically be from about 10 to about 1000, for example from about 10 to about 100.

MCM-68 is generally thermally stable and, in the calcined form, can exhibit a relatively high surface area (e.g., about 660 m$^2$/g with micropore volume of about 0.21 cc/g) and significant hydrocarbon sorption capacity, e.g.:

| | |
|---|---|
| n-Hexane sorption at ~75 torr, ~90° C. | ~10.8 wt % |
| Benzene sorption at ~75 torr, ~30° C. | ~18.8 wt % |
| 2,2-Dimethylbutane sorption at ~60 torr, ~120° C. | ~11.0 wt % |
| Mesitylene sorption at ~2 torr, ~100° C. | ~3.3 wt %. |

In its active, hydrogen form, MCM-68 can exhibit a relatively high acid activity, with an Alpha Value of about 900 to about 2000. Alpha Value is an approximate indication of the catalytic cracking activity of the catalyst compared to a standard catalyst, and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; and in the *Journal of Catalysis*, 4, 527 (1965); 6, 278 (1966); and 61, 395 (1980), each incorporated herein by reference as to that description. The experimental conditions of the test used herein include a constant temperature of ~538° C. and a variable flow rate, as described in detail in the *Journal of Catalysis*, 61, 395 (1980).

As disclosed in U.S. Pat. No. 6,049,018, MCM-68 has previously been synthesized using N,N,N',N'-tetraethylbicyclo[2.2.2]oct-7-ene-2,3:5,6-dipyrrolidinium dications as the structure directing agent. However, the high cost of this structure directing agent has significantly hindered the commercial development of MCM-68.

The present method of synthesizing MCM-68 employs as the structure directing agent cations having the following general structure: $R_1$-$R_3$-$R_2$, where $R_1$ and $R_2$ are the same or different, and where $R_1$ or $R_2$ or both $R_1$ and $R_2$ are an N-alkylpiperidinium group of the formula

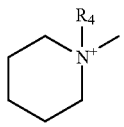

(I)

or where $R_1$ or $R_2$ or both $R_1$ and $R_2$ are a quinuclidinium group of the formula

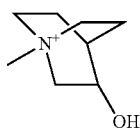

(II)

where $R_3$ is a polymethylene group of the formula $(CH_2)_n$, where n is from 4 to 6, or where $R_3$ is a cycloalkylene group having from 5 to 8 carbon atoms, and where $R_4$ is an alkyl group having 1 to 4 carbon atoms.

Preferred dications can include 3-hydroxy-1-(4-(1-methylpiperidin-1-ium-1-yl)butyl)quinuclidin-1-ium, 3-hydroxy-1-(5-(1-methylpiperidin-1-ium-1-yl)pentyl)quinuclidin-1-ium, 1,1'-(butane-1,4-diyl)bis(1-methylpiperidin-1-ium), 1,1'-(pentane-1,5-diyl)bis(1-methylpiperidin-1-ium), 1,1'-(hexane-1,6-diyl)bis(1-methylpiperidin-1-ium), and 1,1'-((3as,6as)-octahydropentalene-2,5-diyl)bis(1-methylpiperidin-1-ium).

1,1'-(hexane-1,6-diyl)bis(1-methylpiperidin-1-ium)dications have been used to direct the synthesis of the zeolite IZM-2 (see, e.g., PCT Publication No. WO 2010/015732 and U.S. Patent Application Publication No. 2010/0272624), and 1,1'-(pentane-1,5-diyl)bis(1-methylpiperidin-1-ium)dications have been used to direct the synthesis of the zeolite IZM-3 (see, e.g., PCT Publication No. WO 2009/090336). However, as with many other structure directing agent systems, it has now been found that, by varying the synthesis conditions, 1,1'-(hexane-1,6-diyl)bis(1-methylpiperidin-1-ium)dications and 1,1'-(pentane-1,5-diyl)bis(1-methylpiperidin-1-ium)dications, can be effective in directing the synthesis of different molecular sieve materials, and in particular can be effective in directing the synthesis of rather pure phase MCM-68.

In the present method, a reaction mixture is produced comprising a source of water, a source of an oxide of a tetravalent element, Y, selected from at least one of silicon, tin, titanium, vanadium, and germanium, a source of an oxide of trivalent element, X, selected from at least one of aluminum, boron, gallium, iron, and chromium, a source of an alkali or alkaline earth metal, M, together with a source of Q cations. Generally, the composition of the reaction mixture can be controlled so that the molar ratio $Q/YO_2$ in said reaction mixture is in the range from about 0.01 to about 1, such as from about 0.05 to about 0.5. More specifically, the reaction mixture can have a composition, in terms of mole ratios of oxides, within the following ranges:

| Reactants | Useful | Preferred |
|---|---|---|
| $YO_2/X_2O_3$ | ~4 to ~200 | ~8 to ~120 |
| $H_2O/YO_2$ | ~5 to ~200 | ~14 to ~50 |
| $OH^-/YO_2$ | ~0.05 to ~1 | ~0.10 to ~0.53 |
| $M/YO_2$ | ~0.05 to ~2 | ~0.15 to ~0.9 |
| $Q/YO_2$ | ~0.01 to ~1 | ~0.05 to ~0.7 |

The reaction mixture may optionally also comprise seeds of MSE framework type molecular sieve, such as MCM-68, for example, such that the weight ratio of seeds/$YO_2$ in the reaction mixture can be between about 0.001 and about 0.3, such as between about 0.01 and about 0.08 or between about 0.01 and about 0.05. However, such seeds are not necessary and may be specifically omitted in certain embodiments.

The tetravalent element, Y, may comprise or be silicon, the trivalent element, X, may comprise or be aluminum, and the alkali or alkaline earth metal, M, may comprise at least one of sodium and potassium. When the alkali or alkaline earth metal, M, comprises potassium, the molar ratio of Na to the total metal M may be from 0 to about 0.9, for example, from 0 to about 0.5.

Suitable sources of silicon oxide that can be used to produce the reaction mixture described above can include, but are not limited to, colloidal silica, precipitated silica, potassium silicate, sodium silicate, fumed silica, and the like, as well as combinations thereof. Suitable sources of aluminum oxide can include, but are not limited to, hydrated aluminum oxides, such as boehmite, gibbsite, and pseudoboehmite, especially gibbsite, as well as oxygen-containing aluminum salts, such as aluminum nitrate, and the like, as well as combinations thereof. Suitable sources of alkali metal can include sodium and/or potassium hydroxide.

Suitable sources of dication structure directing agents can include any salts of these dications which are not detrimental to the formation of the crystalline material MCM-68, for example, halides (e.g., iodides) and/or hydroxides.

Irrespective of the source of cations, Q, when the reaction mixture has been prepared, crystallization to produce the desired MCM-68 can be conducted under either static or stirred conditions in a suitable reactor vessel, such as for example, polypropylene jars or stainless steel autoclaves optionally lined with Teflon®, e.g., at a temperature between about 100° C. and about 200° C. for up to about 28 days, such as at a temperature between about 145° C. and about 175° C. for about 24 hours to about 170 hours. Thereafter, the crystals can be separated from the liquid and recovered.

The product of the synthesis reaction can advantageously comprise or be a crystalline molecular sieve having the MSE framework type and containing within its pore structure the dication structure directing agent. The resultant as-synthesized material can have an X-ray diffraction pattern distinguishable from the patterns of other known as-synthesized or thermally treated crystalline materials, such as having the lines listed in Table 2 below.

TABLE 2

| d(Å) | Relative Intensity [100 × I/I(o)] |
|---|---|
| 13.56 +/− 0.39 | VW |
| 12.93 +/− 0.37 | M-S |
| 10.92 +/− 0.31 | W |

TABLE 2-continued

| d(Å) | Relative Intensity [100 × I/I(o)] |
|---|---|
| 10.16 +/− 0.29 | VW-W |
| 9.15 +/− 0.26 | VW-W |
| 8.19 +/− 0.23 | VW |
| 4.58 +/− 0.13 | W |
| 4.54 +/− 0.13 | W |
| 4.44 +/− 0.12 | W |
| 4.32 +/− 0.12 | VW |
| 4.23 +/− 0.12 | VW |
| 4.10 +/− 0.12 | VS |
| 4.06 +/− 0.12 | M |
| 3.98 +/− 0.11 | W |
| 3.88 +/− 0.11 | M |
| 3.80 +/− 0.11 | VW |
| 3.40 +/− 0.10 | VW |
| 3.24 +/− 0.09 | W |
| 2.90 +/− 0.08 | VW |

Again, these X-ray diffraction data were collected on similar equipment and in a similar manner as those listed in Table 1 hereinabove.

As-synthesized crystalline molecular sieve containing dications within its pore structure can normally be activated before use in such a manner as to substantially remove the organic structure directing agent from the molecular sieve, leaving active catalytic sites within the microporous channels of the molecular sieve open for contact with a feedstock. The activation process can typically be accomplished by heating the molecular sieve at a temperature from about 200° C. to about 800° C. for an appropriate period of time in the presence of an oxygen-containing gas.

To the extent desired, the original sodium and/or potassium cations of the as-synthesized material can be replaced in accordance with techniques well known in the art, at least in part, e.g., by ion exchange with other cations, which can include, but are not limited to metal ions, hydrogen ions, hydrogen ion precursors, e.g., ammonium ions, and the like, and mixtures thereof. Particularly preferred exchange cations, when present, can include those that can tailor the catalytic activity for certain hydrocarbon conversion reactions (e.g., hydrogen, rare earth metals, and metals of Groups 2, 3, 4, 5, 6, 7, 8, 9, 10, 11, 12, and 13 of the Periodic Table of the Elements.

The crystalline molecular sieve produced by the present process can be used to catalyze a wide variety of organic compound conversion processes including many of present commercial/industrial importance. Examples of chemical conversion processes effectively catalyzed by the crystalline material of this invention, by itself or in combination with one or more other catalytically active substances including other crystalline catalysts, can include those requiring a catalyst with acid activity. Specific examples can include, but are not limited to:

(a) alkylation of aromatics with short chain ($C_2$-$C_6$) olefins, e.g., alkylation of ethylene or propylene with benzene to produce ethylbenzene or cumene respectively, in the gas or liquid phase, with reaction conditions optionally including one or more of a temperature from about 10° C. to about 250° C., a pressure from about 0 psig to about 500 psig (about 3.5 MPag), a total weight hourly space velocity (WHSV) from about 0.5 $hr^{-1}$ to about 100 $hr^{-1}$, and an aromatic/olefin mole ratio from about 0.1 to about 50;

(b) alkylation of aromatics with long chain ($C_{10}$-$C_{20}$) olefins, in the gas or liquid phase, with reaction conditions optionally including one or more of a temperature from about 250° C. to about 500° C., a pressure from about 0 psig to 500 psig (about 3.5 MPag), a total WHSV from about 0.5 $hr^{-1}$ to about 50 $hr^{-1}$, and an aromatic/olefin mole ratio from about 1 to about 50;

(c) transalkylation of aromatics, in gas or liquid phase, e.g., transalkylation of polyethylbenzenes and/or polyisopropylbenzenes with benzene to produce ethylbenzene and/or cumene respectively, with reaction conditions optionally including one or more of a temperature from about 100° C. to about 500° C., a pressure from about 1 psig (about 7 kPag) to about 500 psig (about 3.5 MPag), and a WHSV from about 1 $hr^{-1}$ to about 10,000 $hr^{-1}$;

(d) disproportionation of alkylaromatics, e.g., disproportionation of toluene to produce xylenes, with reaction conditions optionally including one or more of a temperature from about 200° C. to about 760° C., a pressure from about 1 atm (about 0 psig) to about 60 atm (about 5.9 MPag), a WHSV from about 0.1 $hr^{-1}$ to about 20 $hr^{-1}$, and a hydrogen/hydrocarbon mole ratio from 0 (no added hydrogen) to about 50;

(e) dealkylation of alkylaromatics, e.g., deethylation of ethylbenzene, with reaction conditions optionally including one or more of a temperature from about 200° C. to about 760° C., a pressure from about 1 atm (about 0 psig) to about 60 atm (about 5.9 MPag), a WHSV from about 0.1 $hr^{-1}$ to about 20 $hr^{-1}$, and a hydrogen to hydrocarbon mole ratio from 0 (no added hydrogen) to about 50;

(f) isomerization of alkylaromatics, such as xylenes, with reaction conditions optionally including one or more of a temperature from about 200° C. to about 540° C., a pressure from about 100 kPaa to about 7 MPaa, a WHSV from about 0.1 $hr^{-1}$ to about 50 $hr^{-1}$, and a hydrogen/hydrocarbon mole ratio from 0 (no added hydrogen) to about 10;

(g) reaction of paraffins with aromatics, e.g., to form alkylaromatics and light gases, with reaction conditions optionally including one or more of a temperature from about 260° C. to about 375° C., a pressure from about 0 psig to about 1000 psig (about 6.9 MPag), a WHSV from about 0.5 $hr^{-1}$ to about 10 $hr^{-1}$, and a hydrogen/hydrocarbon mole ratio from 0 (no added hydrogen) to about 10;

(h) paraffin isomerization to provide branched paraffins with reaction conditions optionally including one or more of a temperature from about 200° C. to about 315° C., a pressure from about 100 psig (about 690 kPag) to about 1000 psig (about 6.9 MPag), a WHSV from about 0.5 $hr^{-1}$ to about 10 $hr^{-1}$, and a hydrogen to hydrocarbon mole ratio from about 0.5 to about 10;

(i) alkylation of iso-paraffins, such as isobutane, with olefins, with reaction conditions optionally including one or more of a temperature from about −20° C. to about 350° C., a pressure from about 0 psig to about 700 psig (about 4.9 MPag), and a total olefin WHSV from about 0.02 $hr^{-1}$ to about 10 $hr^{-1}$;

(j) dewaxing of paraffinic feeds with reaction conditions optionally including one or more of a temperature from about 200° C. to about 450° C., a pressure from about 0 psig to about 1000 psig (about 6.9 MPag), a WHSV from about 0.2 $hr^{-1}$ to about 10 $hr^{-1}$, and a hydrogen/hydrocarbon mole ratio from about 0.5 to about 10;

(k) cracking of hydrocarbons with reaction conditions optionally including one or more of a temperature from about 300° C. to about 700° C., a pressure from about 0.1 atm (about 10 kPag) to about 30 atm (about 3 MPag), and a WHSV from about 0.1 $hr^{-1}$ to about 20 $hr^{-1}$;

(l) isomerization of olefins with reaction conditions optionally including one or more of a temperature from about 250° C. to about 750° C., an olefin partial pressure from about 30 kPa to about 300 kPa, and a WHSV from about 0.5 $hr^{-1}$ to about 500 $hr^{-1}$; and (m) a hydrocarbon trap (e.g., pre-catalytic converter adsorbent) for cold start emissions in motor vehicles.

As described in U.S. Pat. No. 7,198,711, MCM-68 may be used as an additive component in conjunction with a conventional cracking catalyst, such as a large pore molecular sieve having a pore size greater than about 7 Angstroms.

As in the case of many catalysts, it may be desirable to incorporate the molecular sieve produced by the present process with another material resistant to the temperatures and other conditions employed in organic conversion processes. Such materials can include active and inactive materials and synthetic or naturally occurring zeolites, as well as inorganic materials such as clays, silica, and/or metal oxides such as alumina. The latter may be naturally occurring and/or in the form of gelatinous precipitates/gels including mixtures of silica and metal oxides. Use of a material in conjunction with the molecular sieve produced by the present process (i.e., combined therewith and/or present during synthesis of the new crystal), which is active, can tend to change the conversion capability and/or selectivity of the catalyst in certain organic conversion processes. Inactive materials suitably tend to serve merely as diluents, e.g., to control the amount of conversion in a given process so that products can be obtained economically and orderly, for instance without employing too many other means for controlling the rate of reaction. These inventive materials may be incorporated into naturally occurring clays, e.g., bentonite and/or kaolin, to improve the crush strength of the catalyst under commercial operating conditions. Said materials (i.e., clays, oxides, etc.) can additionally or alternately function as binders for the catalyst. It can be desirable to provide a catalyst having good crush strength, because, in commercial use, it can often be desirable to prevent the catalyst from breaking down into powder-like materials. These clay and/or oxide binders have been employed normally only for the purpose of improving the crush strength of the catalyst.

Naturally occurring clays that can be composited with the molecular sieve produced by the present process can include, but are not limited to, the montmorillonite and kaolin families, which include the subbentonites and the kaolins commonly known as Dixie, McNamee, Georgia, and Florida clays and/or others in which the main mineral constituent can be halloysite, kaolinite, dickite, nacrite, and/or anauxite. Such clays can be used in the raw state as originally mined and/or initially subjected to calcination, acid treatment, and/or chemical modification. Binders useful for compositing with the molecular sieve produced by the present process can additionally or alternately include inorganic oxides, such as silica, zirconia, titania, magnesia, beryllia, alumina, and mixtures thereof.

Additionally or alternately, the molecular sieve produced by the present process can be composited with a porous matrix material such as silica-alumina, silica-magnesia, silica-zirconia, silica-thoria, silica-beryllia, silica-titania, and/or ternary compositions such as silica-alumina-thoria, silica-alumina-zirconia silica-alumina-magnesia, and silica-magnesia-zirconia.

The relative proportions of finely divided crystalline molecular sieve material and inorganic oxide matrix vary widely, with the crystal content ranging from about 1% to about 90% by weight and more usually, particularly when the composite is prepared in the form of beads or extrudates, ranging from about 2% to about 80% by weight of the composite.

Additionally or alternately, the present invention can include one or more of the following embodiments.

Embodiment 1

A method of synthesizing a crystalline molecular sieve having an MSE framework type, the method comprising crystallizing a reaction mixture comprising a source of water, a source of an oxide of a tetravalent element, Y, selected from at least one of silicon, tin, titanium, vanadium, and germanium, optionally a source of a trivalent element, X, a source of an alkali or alkaline earth metal, M, and a source of organic cations, Q, having the following general structure: $R_1$-$R_3$-$R_2$, where $R_1$ and $R_2$ are the same or different, and where $R_1$ or $R_2$ or both $R_1$ and $R_2$ are an N-alkylpiperidinium group of the formula

or where $R_1$ or $R_2$ or both $R_1$ and $R_2$ are a quinuclidinium group of the formula

where $R_3$ is a polymethylene group of the formula $(CH_2)_n$, where n is from 4 to 6, or where $R_3$ is a cycloalkylene group having from 5 to 8 carbon atoms, and where $R_4$ is an alkyl group having 1 to 4 carbon atoms, for example a methyl group.

Embodiment 2

The method of embodiment 1, wherein $R_1$ and $R_2$ are both an N-alkylpiperidinium group of the formula

Embodiment 3

The method of embodiment 1, wherein $R_1$ is an N-alkylpiperidinium group of the formula

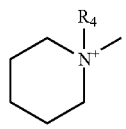
(I)

where $R_2$ is a quinuclidinium group of the formula

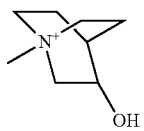
(II)

and where n is 4 or 5.

Embodiment 4

The method of any one of the previous embodiments, wherein the molar ratio $Q/YO_2$ in said reaction mixture is in a range from about 0.01 to about 1.0, for example from about 0.05 to about 0.7.

Embodiment 5

The method of any one of the previous embodiments, wherein said reaction mixture comprises a source of an oxide of trivalent element, X, selected from at least one of aluminum, boron, gallium, iron and chromium.

Embodiment 6

The method of embodiment 5, wherein a molar ratio $YO_2/X_2O_3$ in said reaction mixture is in a range from about 4 to about 200, for example from about 8 to about 120.

Embodiment 7

The method of embodiment 5 or embodiment 6, wherein the reaction mixture has the following molar composition:

| | |
|---|---|
| $YO_2/X_2O_3$ | ~4 to ~200 |
| $H_2O/YO_2$ | ~5 to ~200 |
| $OH^-/YO_2$ | ~0.05 to ~1 |
| $M/YO_2$ | ~0.05 to ~2 |
| $Q/YO_2$ | ~0.01 to ~1. |

Embodiment 8

The method of any one of embodiments 5-7, wherein the reaction mixture has the following molar composition:

| | |
|---|---|
| $YO_2/X_2O_3$ | ~8 to ~120 |
| $H_2O/YO_2$ | ~14 to ~50 |
| $OH^-/YO_2$ | ~0.10 to ~0.53 |
| $M/YO_2$ | ~0.15 to ~0.9 |
| $Q/YO_2$ | ~0.05 to ~0.7. |

Embodiment 9

The method of any one of the previous embodiments, wherein said tetravalent element, Y, is silicon and said trivalent element, X, is aluminum.

Embodiment 10

The method of any one of the previous embodiments, wherein said alkali or alkaline earth metal, M, is potassium.

Embodiment 11

The method of any one of the previous embodiments, wherein said reaction mixture does not comprise seeds of an MSE framework type molecular sieve.

Embodiment 12

The method of any one of the previous embodiments, wherein the crystallizing is conducted at a temperature between about 100° C. and about 200° C. for up to about 28 days, for example between about 145° C. and about 175° C. for between about 24 hours and about 170 hours.

Embodiment 13

The method of any one of the previous embodiments, wherein Q is a 3-hydroxy-1-(4-(1-methylpiperidin-1-ium-1-yl)butyl)quinuclidin-1-ium dication of the formula

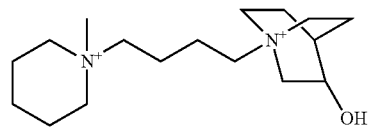
(III)

or wherein Q is a 3-hydroxy-1-(5-(1-methylpiperidin-1-ium-1-yl)pentyl)quinuclidin-1-ium dication of the formula

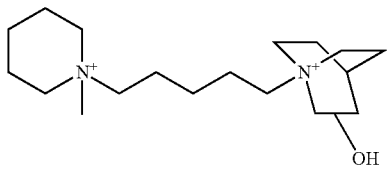
(IV)

or wherein Q is a 1,1'-(butane-1,4-diyl)bis(1-methylpiperidin-1-ium)dication of the formula

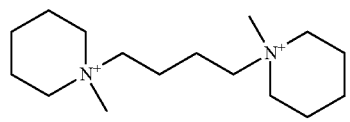
(V)

or wherein Q is a 1,1'-(pentane-1,5-diyl)bis(1-methylpiperidin-1-ium)dication of the formula

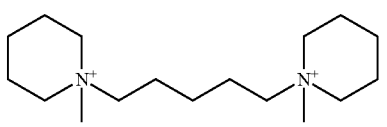
(VI)

or wherein Q is a 1,1'-(hexane-1,6-diyl)bis(1-methylpiperidin-1-ium)dication of the formula

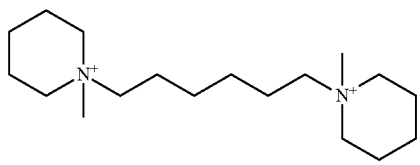
(VII)

or wherein Q is a 1,1'-((3as,6as)-octahydropentalene-2,5-diyl)bis(1-methylpiperidin-1-ium)dication of the formula

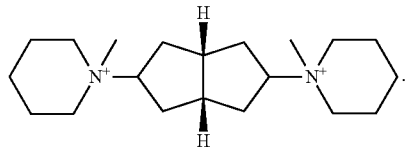
(VIII)

Embodiment 14

A crystalline molecular sieve having an MSE framework type and containing within its pore structure a dication comprising a 3-hydroxy-1-(4-(1-methylpiperidin-1-ium-1-yl)butyl)quinuclidin-1-ium, a 1-(5-(1-methylpiperidin-1-ium-1-yl)pentyl)quinuclidin-1-ium, a 1,1'-(butane-1,4-diyl)bis(1-methylpiperidin-1-ium), a 1,1'-(pentane-1,5-diyl)bis(1-methylpiperidin-1-ium), a 1,1'-(hexane-1,6-diyl)bis(1-methylpiperidin-1-ium), or a 1,1'-((3as,6as)-octahydropentalene-2,5-diyl)bis(1-methylpiperidin-1-ium).

Embodiment 15

A dication of the structure $R_1$-$R_3$-$R_2$, where $R_1$ is an N-alkylpiperidinium group of the formula

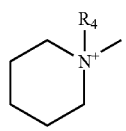
(I)

where $R_2$ is a quinuclidinium group of the formula

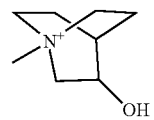
(II)

where $R_3$ is a polymethylene group of the formula $(CH_2)_n$, where n is from 4 to 6, and where $R_4$ is an alkyl group having 1 to 4 carbon atoms.

Embodiment 16

A dication of embodiment 15, which is a 3-hydroxy-1-(4-(1-methylpiperidin-1-ium-1-yl)butyl)quinuclidin-1-ium dication of Formula (III) or a 3-hydroxy-1-(5-(1-methylpiperidin-1-ium-1-yl)pentyl)quinuclidin-1-ium dication of Formula (IV).

Embodiment 17

A 1,1'-((3as,6as)-octahydropentalene-2,5-diyl)bis(1-methylpiperidin-1-ium)dication.

EXAMPLES

In order to more fully illustrate the nature of the invention and the manner of practicing same, the following examples are presented.

Example 1

Synthesis of 1-(4-bromobutyl)-1-methylpiperidin-1-ium bromide

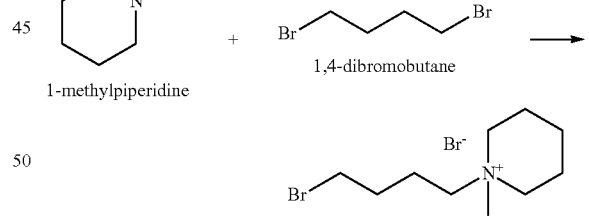

A solution of 1-methylpiperidine (~24.80 g) in anhydrous dimethylformamide (~500 mL) was added slowly to a solution of 1,4-dibromobutane (~269.9 g) in anhydrous dimethylformamide (~250 mL) over the course of about 24 hours under a nitrogen atmosphere with rapid stirring. Stirring of the solution was continued for a further ~48 hours. The reaction mixture was then passed through a D-frit (~10-20 microns) to separate any solid 1,1'-(butane-1,4-diyl)bis(1-methylpiperidin-1-ium) bromide impurity. Anhydrous diethyl ether (~2000 mL) was then added to the filtrate to precipitate the product which was then filtered using a D-frit and rinsed with anhydrous diethyl ether (3×~400 mL). After drying the product (~63.7 g, ~80%) was confirmed to be 1-(4-bromobutyl)-1-methylpiperidin-1-ium bromide by ¹H NMR.

Example 2

Synthesis of 3-hydroxy-1-(4-(1-methylpiperidin-1-ium-1-yl)butyl)quinuclidin-1-ium bromide

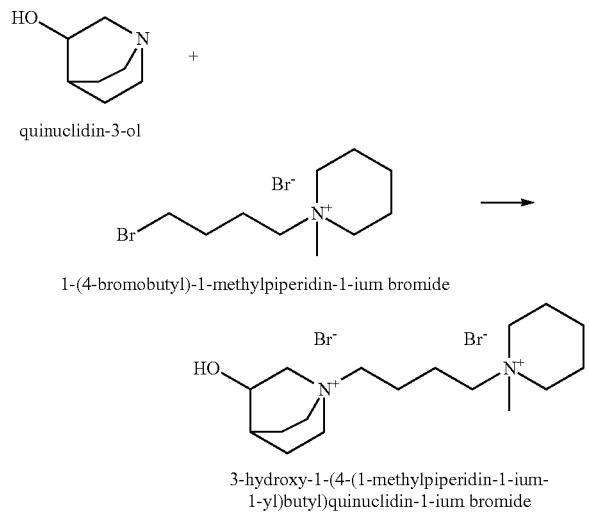

Dimethylformamide (~700 mL), 1-(4-bromobutyl)-1-methylpiperidin-1-ium bromide (~65.16 g) and 3-quinuclidinol (~27.62 g) were combined and stirred at room temperature (about 20-25° C.) overnight. The solid product was filtered and then washed with diethyl ether (3×~100 mL). After drying the product (~81.4 g, ~89%) was confirmed to be 3-hydroxy-1-(4-(1-methylpiperidin-1-ium-1-yl)butyl)quinuclidin-1-ium bromide by ¹H NMR.

Example 3

Synthesis of 3-hydroxy-1-(4-(1-methylpiperidin-1-ium-1-yl)butyl)quinuclidin-1-ium hydroxide 3-hydroxy-1-(4-(1-methylpiperidin-1-ium-1-yl)butyl)quinuclidin-1-ium bromide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt %. The concentration was confirmed by acid-base titration and by 1H NMR.

Example 4

Synthesis of 1-(5-bromopentyl)-1-methylpiperidin-1-ium bromide

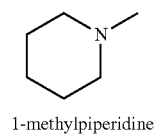

1-methylpiperidine

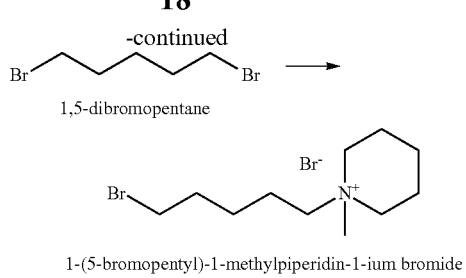

A solution of 1-methylpiperidine (~26.04 g) in dimethylformamide (~250 mL) was added slowly to a solution of 1,5-dibromopentane (~226.3 g) in dimethylformamide (~50 mL) with rapid stirring. Stirring of the solution was continued overnight. The reaction mixture was then poured into diethyl ether (~1500 mL) producing a yellow oil. The diethyl ether was decanted and the oil poured into a solution of fresh diethyl ether (~1500 mL) with acetone (~250 mL) and then stirred overnight. The resulting waxy solid was filtered. After drying the product (~51.8 g, ~60%) was confirmed to be 1-(5-bromopentyl)-1-methylpiperidin-1-ium bromide by ¹H NMR.

Example 5

Synthesis of 3-hydroxy-1-(5-(1-methylpiperidin-1-ium-1-yl)pentyl)quinuclidin-1-ium bromide

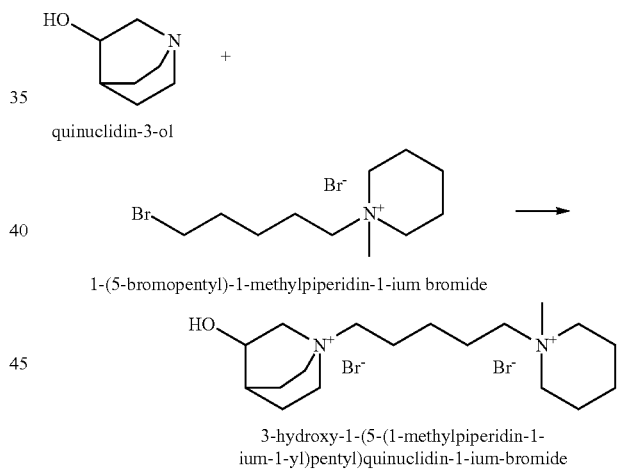

Dimethylformamide (~450 mL), 1-(5-bromopentyl)-1-methylpiperidin-1-ium bromide (~59.84 g) and 3-quinuclidinol (~25.03 g) were combined and stirred at room temperature for about 5 days. The solid product was filtered and then washed with diethyl ether (3×~100 mL). After drying the product (~61.3 g, ~74%) was confirmed to be 3-hydroxy-1-(5-(1-methylpiperidin-1-ium-1-yl)pentyl)quinuclidin-1-ium bromide by ¹H NMR.

Example 6

Synthesis of 3-hydroxy-1-(5-(1-methylpiperidin-1-ium-1-yl)pentyl)quinuclidin-1-ium hydroxide 3-hydroxy-1-(5-(1-methylpiperidin-1-ium-1-yl)pentyl)quinuclidin-1-ium bromide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt %. The concentration was confirmed by acid-base titration and by $^1$H NMR.

Example 7

Synthesis of 1,1'-(butane-1,4-diyl)bis(1-methylpiperidin-1-ium) bromide

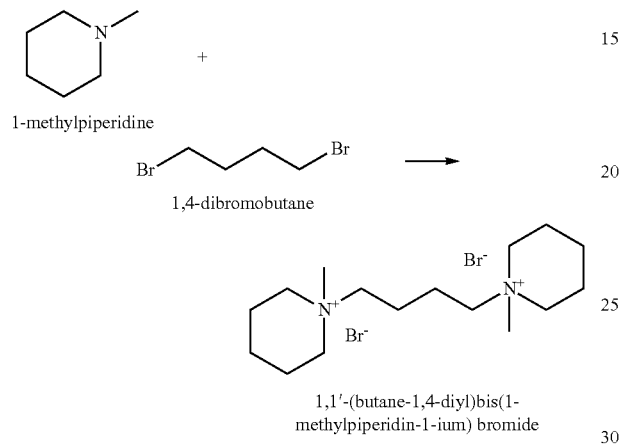

1,1'-(butane-1,4-diyl)bis(1-methylpiperidin-1-ium) bromide 1-methylpiperidine (~75.67 g), 1,4-dibromobutane (~75 g), and dimethylformamide (~250 mL) were combined and stirred at room temperature for ~24 hours. The solid product was filtered and then washed with diethyl ether (~750 mL). After drying the product (~115.8 g, ~81%) was confirmed to be 1,1'-(butane-1,4-diyl)bis(1-methylpiperidin-1-ium) bromide by $^1$H NMR.

Example 8

Synthesis of 1,1'-(butane-1,4-diyl)bis(1-methylpiperidin-1-ium) hydroxide 1,1'-(butane-1,4-diyl)bis(1-methylpiperidin-1-ium) bromide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt %. The concentration was confirmed by acid-base titration and by $^1$H NMR.

Example 9

Synthesis of 1,1'-(pentane-1,5-diyl)bis(1-methylpiperidin-1-ium) bromide

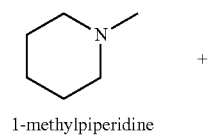

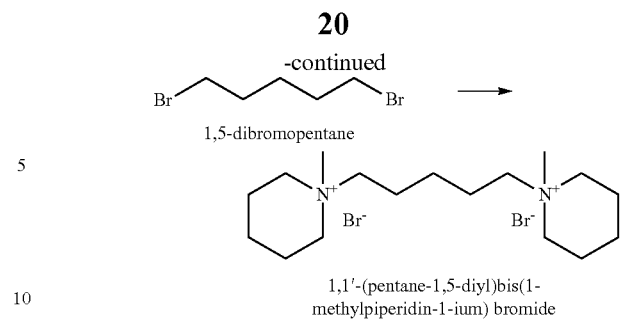

1,1'-(pentane-1,5-diyl)bis(1-methylpiperidin-1-ium) bromide 1-methylpiperidine (~71.2 g), 1,4-dibromopentane (~75 g), and dimethylformamide (~250 mL) were combined and stirred at room temperature for about 24 hours. The solid product was filtered and then washed with diethyl ether (~750 mL). After drying the product (~108.5 g, ~78%) was confirmed to be 1,1'-(pentane-1,5-diyl)bis(1-methylpiperidin-1-ium) bromide by $^1$H NMR.

Example 10

Synthesis of 1,1'-(pentane-1,5-diyl)bis(1-methylpiperidin-1-ium) hydroxide 1,1'-(pentane-1,5-diyl)bis(1-methylpiperidin-1-ium) bromide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt %. The concentration was confirmed by acid-base titration and by $^1$H NMR.

Example 11

Synthesis of 1,1'-(hexane-1,6-diyl)bis(1-methylpiperidin-1-ium) bromide

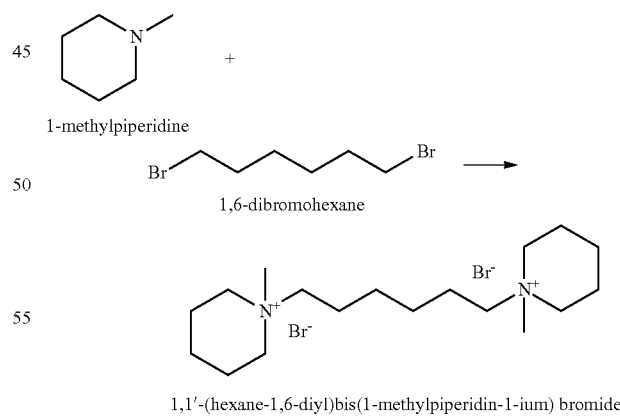

1,1'-(hexane-1,6-diyl)bis(1-methylpiperidin-1-ium) bromide 1-methylpiperidine (~73.3 g), 1,4-dibromohexane (~82 g), and dimethylformamide (~250 mL) were combined and stirred at room temperature for about 24 hours. The solid product was filtered and then washed with diethyl ether (~750 mL). After drying the product (~106 g, ~71%) was confirmed to be 1,1'-(hexane-1,6-diyl)bis(1-methylpiperidin-1-ium) bromide by $^1$H NMR.

Example 12

Synthesis of 1,1'-(hexane-1,6-diyl)bis(1-methylpiperidin-1-ium) hydroxide 1,1'-(hexane-1,6-diyl)bis(1-methylpiperidin-1-ium) bromide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt %. The concentration was confirmed by acid-base titration and by $^1$H NMR.

Example 13

Synthesis of (3as,6as)-2,5-di(piperidin-1-yl)octahydropentalene

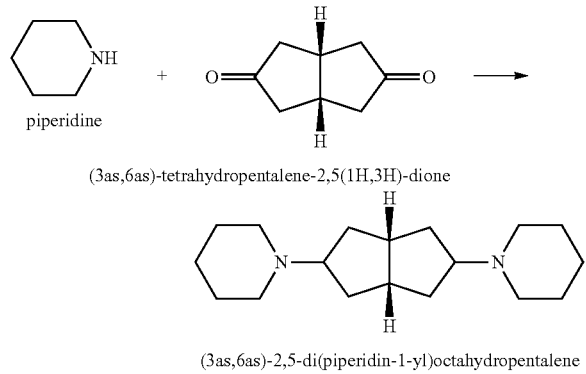

Anhydrous tetrahydrofuran (~150 mL), piperidine (~5.43 g), and (3as,6as)-tetrahydropentalene-2,5(1H,3H)-dione (~5.29 g) were combined and stirred thoroughly at room temperature (about 20-25° C.). Then sodium triacetoxyborohydride (~21.64 g) was added and the mixture was stirred at room temperature for about one day. Aqueous sodium hydroxide (~25 g, ~25 wt %) was then added and the solution extracted with petroleum ether (3×~100 mL). The organic extracts were combined and washed with deionized water (2×~150 mL) and saturated sodium chloride (2×~150 mL). The resulting solid product was filtered and after drying the product (~5.71 g, ~32%) was confirmed to be (3as,6as)-2,5-di(piperidin-1-yl)octahydropentalene by $^1$H NMR.

Example 14

Synthesis of 1,1'-((3as,6as)-octahydropentalene-2,5-diyl)bis(1-methylpiperidin-1-ium) iodide

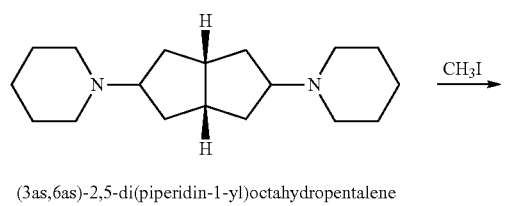

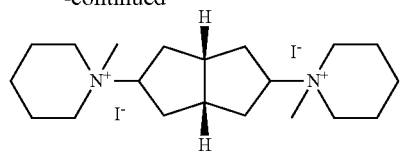

1,1'-((3as,6as)-octahydropentalene-2,5-diyl)bis(1-methylpiperidin-1-ium)iodide

Dimethylformamide (~50 mL) and (3as,6as)-2,5-di(piperidin-1-yl)octahydropentalene (~5.69 g) were combined and stirred. Then iodomethane (~6.43 g) was added, and the mixture was left at room temperature (about 20-25° C.) overnight without stirring. The solid product was filtered and the filtrate was slowly added to stirred diethyl ether (~500 mL) producing a solid precipitate. After drying the combined solid product (~11.3 g, ~98%) was confirmed to be 1,1'-((3as,6as)-octahydropentalene-2,5-diyl)bis(1-methylpiperidin-1-ium) iodide by $^1$H NMR.

Example 15

Synthesis of 1,1'-((3as,6as)-octahydropentalene-2,5-diyl)bis(1-methylpiperidin-1-ium) hydroxide 1,1'-((3as,6as)-octahydropentalene-2,5-diyl)bis(1-methylpiperidin-1-ium) iodide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt %. The concentration was confirmed by acid-base titration and by $^1$H NMR.

Example 16

Synthesis of MCM-68

A gel was prepared by mixing together deionized water (~2 μL), aqueous CAB-O-SPERSE 2017A (~162 μL, ~17 wt %), aqueous 3-hydroxy-1-(5-(1-methylpiperidin-1-ium-1-yl)pentyl)quinuclidin-1-ium hydroxide (~189 μL, ~25.1 wt %), aqueous potassium hydroxide (~42 μL, ~17.5 wt %), and aqueous aluminum nitrate (~64 μL, ~15 wt %). The starting gel had the following molar ratios

| | |
|---|---|
| Si/Al | ~10 |
| OH$^-$/Si | ~0.6 |
| SDA/Si | ~0.3 |
| K/Si | ~0.3 |
| Water/Si | ~44 | where SDA is the 3-hydroxy-1-(5-(1-methylpiperidin-1-ium-1-yl)pentyl)quinuclidin-1-ium structure directing agent. The mixture was stirred until homogenous and then reacted at autogenous pressure at about 160° C. for about 7 days in an air oven with tumbling. The product was centrifuged, washed three times with deionized water, dried, and then subjected to powder X-ray diffraction analysis. The X-ray diffraction pattern showed the product to be pure MCM-68 zeolite.

Example 17

Synthesis of MCM-68

A gel was prepared by mixing together deionized water (~24 μL), UltraSil™ precipitated silica (~44 mg, ~92.7 wt %), aqueous 3-hydroxy-1-(5-(1-methylpiperidin-1-ium-1-yl)pentyl)quinuclidin-1-ium hydroxide (~256 μL, ~25.1 wt %), aqueous potassium hydroxide (~56 μL, ~17.5 wt %), and aqueous aluminum nitrate (~86 μL, ~15 wt %). The starting gel had the following molar ratios

| | |
|---|---|
| Si/Al | ~10 |
| OH$^-$/Si | ~0.6 |
| SDA/Si | ~0.3 |
| K/Si | ~0.3 |
| Water/Si | ~30 | where SDA is the 3-hydroxy-1-(5-(1-methylpiperidin-1-ium-1-yl)pentyl)quinuclidin-1-ium structure directing agent. The mixture was stirred until homogenous and then reacted at autogenous pressure at about 160° C. for about 10 days in an air oven with tumbling. The product was centrifuged, washed three times with deionized water, dried, and then subjected to powder X-ray diffraction analysis. The X-ray diffraction pattern showed the product to be pure MCM-68 zeolite.

Example 18

Synthesis of MCM-68

A gel was prepared by mixing together deionized water (~5 μL), aqueous LUDOX SM-30 (~97 μL, ~30.1 wt %), aqueous 3-hydroxy-1-(5-(1-methylpiperidin-1-ium-1-yl)pentyl)quinuclidin-1-ium hydroxide (~223 μL, ~25.1 wt %), aqueous potassium hydroxide (~49 μL, ~17.5 wt %), and aqueous aluminum nitrate (~75 μL, ~15 wt %). The starting gel had the following molar ratios

| | |
|---|---|
| Si/Al | ~10 |
| OH$^-$/Si | ~0.6 |
| SDA/Si | ~0.3 |
| K/Si | ~0.3 |
| Water/Si | ~36 | where SDA is the 3-hydroxy-1-(5-(1-methylpiperidin-1-ium-1-yl)pentyl)quinuclidin-1-ium structure directing agent. The mixture was stirred until homogenous and then reacted at autogenous pressure at about 160° C. for about 10 days in an air oven with tumbling. The product was centrifuged, washed three times with deionized water, dried, and then subjected to powder X-ray diffraction analysis. The X-ray diffraction pattern showed the product to be pure MCM-68 zeolite.

Example 19

Synthesis of MCM-68

A gel was prepared by mixing together deionized water (~6 μL), aqueous LUDOX SM-30 (~105 μL, ~30.4 wt %), aqueous 1'-(butane-1,4-diyl)bis(1-methylpiperidin-1-ium) hydroxide (~158 μL, ~20.9 wt %), aqueous sodium hydroxide (~162 μL, ~10 wt %), and aqueous aluminum nitrate (~20 μL, ~15 wt %). The starting gel had the following molar ratios

| | |
|---|---|
| Si/Al | ~40 |
| OH$^-$/Si | ~1 |
| SDA/Si | ~0.19 |
| Na/Si | ~0.7 |
| Water/Si | ~35 | where SDA is the 1'-(butane-1,4-diyl)bis(1-methylpiperidin-1-ium) structure directing agent. The mixture was stirred until homogenous and then reacted at autogenous pressure at about 160° C. for about 7 days in an air oven with tumbling. The product was centrifuged, washed three times with deionized water, dried, and then subjected to powder X-ray diffraction analysis. The X-ray diffraction pattern showed the product to be pure MCM-68 zeolite.

Example 20

Synthesis of MCM-68

A gel was prepared by mixing together deionized water (~5 μL), aqueous LUDOX SM-30 (~70 μL, ~30.4 wt %), aqueous 1,1'-((3as,6as)-octahydropentalene-2,5-diyl)bis(1-methylpiperidin-1-ium) hydroxide (~255 μL, ~5.62 wt %), aqueous potassium hydroxide (~35 μL, ~17.5 wt %), aqueous aluminum nitrate (~90 μL, ~1 wt %), and aqueous hydrochloric acid (~19 μL, ~20 wt %). The starting gel had the following molar ratios

| | |
|---|---|
| Si/Al | ~100 |
| OH$^-$/Si | ~0.2 |
| SDA/Si | ~0.1 |
| K/Si | ~0.3 |
| Water/Si | ~58 | where SDA is the 1,1'-((3as,6as)-octahydropentalene-2,5-diyl)bis(1-methylpiperidin-1-ium) structure directing agent. The mixture was stirred until homogenous and then reacted at autogenous pressure at about 200° C. for about 7 days in an air oven with tumbling. The product was centrifuged, washed three times with deionized water, dried and then subjected to powder X-ray diffraction analysis. The X-ray diffraction pattern showed the product to be pure MCM-68 zeolite. An X-ray diffraction pattern for a sample on MCM-68 prepared in this Example is shown in FIG. 1.

Examples 21 to 74

Further MCM-68 Syntheses

A series of gels were prepared in a manner similar to Examples 16 to 20 above, but having the molar ratios indicated in Table 3 below. The gels were prepared by mixing together deionized water, a Silica Source, aqueous SDA hydroxide, aqueous sodium or potassium hydroxide, aqueous potassium bromide, aqueous aluminum nitrate, and aqueous hydrochloric acid.

In Table 3, the structure directing agent (SDA) is referred to in terms of formulae recited herein. Formula III corresponds to 3-hydroxy-1-(4-(1-methylpiperidin-1-ium-1-yl)butyl)quinuclidin-1-ium hydroxide. Formula IV corresponds to 3-hydroxy-1-(5-(1-methylpiperidin-1-ium-1-yl)pentyl)quinuclidin-1-ium hydroxide. Formula V corresponds to 1,1'-(butane-1,4-diyl)bis(1-methylpiperidin-1-ium) hydroxide. Formula VI corresponds to 1,1'-(pentane-1,5-diyl)bis(1-methylpiperidin-1-ium) hydroxide. Formula VII corresponds to 1,1'-(hexane-1,6-diyl)bis(1-methylpiperidin-1-ium) hydroxide. Formula VIII corresponds to 1,1'-((3as,6as)-octahydropentalene-2,5-diyl)bis(1-methylpiperidin-1-ium) hydroxide.

TABLE 3

| Ex. | Si Source | SDA | Na/Si | K/Si | SDA/Si | OH—/Si | H$_2$O/Si |
|---|---|---|---|---|---|---|---|
| 21 | LUDOX LS-30 | III | 0 | 0.3 | 0.3 | 0.6 | 40 |
| 22 | LUDOX LS-30 | IV | 0 | 0.3 | 0.3 | 0.6 | 36 |
| 23 | LUDOX LS-30 | IV | 0 | 0.45 | 0.3 | 0.75 | 40 |
| 24 | LUDOX SM-30 | IV | 0 | 0.45 | 0.3 | 0.75 | 40 |
| 25 | Cab-O-Sperse | IV | 0 | 0.45 | 0.3 | 0.75 | 49 |
| 26 | Ultrasil | IV | 0 | 0.45 | 0.3 | 0.75 | 33 |
| 27 | LUDOX SM-30 | IV | 0 | 0.45 | 0.3 | 0.75 | 40 |
| 28 | LUDOX SM-30 | IV | 0 | 0.15 | 0.3 | 0.45 | 36 |
| 20 | LUDOX SM-30 | IV | 0 | 0.3 | 0.3 | 0.6 | 38 |
| 30 | LUDOX SM-30 | IV | 0 | 0.3 | 0.4 | 0.75 | 45 |
| 31 | LUDOX SM-30 | IV | 0 | 0.3 | 0.4 | 0.6 | 44 |
| 32 | LUDOX LS-30 | IV | 0 | 0.3 | 0.3 | 0.6 | 36 |
| 33 | Ultrasil | IV | 0 | 0.3 | 0.4 | 0.75 | 35 |
| 34 | LUDOX SM-30 | IV | 0 | 0.15 | 0.3 | 0.45 | 34 |
| 35 | Ultrasil | IV | 0 | 0.15 | 0.4 | 0.6 | 32 |
| 36 | LUDOX SM-30 | IV | 0 | 0.3 | 0.3 | 0.45 | 38 |
| 37 | Ultrasil | IV | 0 | 0.3 | 0.3 | 0.6 | 30 |
| 38 | LUDOX SM-30 | IV | 0 | 0.3 | 0.3 | 0.6 | 36 |
| 39 | LUDOX SM-30 | IV | 0 | 0.3 | 0.4 | 0.75 | 42 |
| 40 | LUDOX SM-30 | IV | 0 | 0.45 | 0.3 | 0.6 | 40 |
| 41 | Ultrasil | IV | 0 | 0.45 | 0.3 | 0.75 | 31 |
| 42 | LUDOX SM-30 | IV | 0 | 0.45 | 0.4 | 0.75 | 46 |
| 43 | Ultrasil | IV | 0 | 0.45 | 0.4 | 0.75 | 39 |
| 44 | LUDOX SM-30 | IV | 0 | 0.15 | 0.3 | 0.45 | 34 |
| 45 | Ultrasil | IV | 0 | 0.45 | 0.4 | 0.75 | 39 |
| 46 | LUDOX SM-30 | IV | 0 | 0.15 | 0.3 | 0.45 | 34 |
| 47 | LUDOX SM-30 | IV | 0 | 0.3 | 0.4 | 0.75 | 42 |
| 48 | Ultrasil | IV | 0 | 0.15 | 0.4 | 0.6 | 32 |
| 49 | Cab-O-Sperse | IV | 0 | 0.3 | 0.4 | 0.6 | 52 |
| 50 | Ultrasil | IV | 0 | 0.15 | 0.3 | 0.45 | 30 |
| 51 | LUDOX SM-30 | IV | 0 | 0.3 | 0.3 | 0.45 | 38 |
| 52 | Ultrasil | IV | 0 | 0.3 | 0.4 | 0.6 | 36 |
| 53 | LUDOX SM-30 | IV | 0 | 0.3 | 0.4 | 0.45 | 50 |
| 54 | Ultrasil | IV | 0 | 0.3 | 0.4 | 0.75 | 35 |
| 55 | LUDOX SM-30 | IV | 0 | 0.3 | 0.4 | 0.6 | 44 |
| 56 | LUDOX LS-30 | IV | 0 | 0.15 | 0.4 | 0.6 | 40 |
| 57 | LUDOX LS-30 | IV | 0 | 0.3 | 0.3 | 0.6 | 36 |
| 58 | Cab-O-Sperse | IV | 0 | 0.3 | 0.3 | 0.6 | 45 |
| 59 | LUDOX LS-30 | IV | 0 | 0.3 | 0.4 | 0.6 | 44 |
| 60 | LUDOX LS-30 | IV | 0 | 0.3 | 0.4 | 0.75 | 42 |
| 61 | Cab-O-Sperse | IV | 0 | 0.3 | 0.4 | 0.75 | 51 |
| 62 | LUDOX SM-30 | VI | 0 | 0.3 | 0.4 | 0.6 | 49 |
| 63 | LUDOX SM-30 | VI | 0 | 0.3 | 0.3 | 0.6 | 40 |
| 64 | LUDOX SM-30 | VI | 0 | 0.3 | 0.4 | 0.75 | 47 |
| 65 | LUDOX SM-30 | VI | 0 | 0.45 | 0.4 | 0.75 | 51 |
| 66 | LUDOX SM-30 | VI | 0 | 0.15 | 0.3 | 0.45 | 37 |
| 67 | Ultrasil | VI | 0 | 0.15 | 0.3 | 0.45 | 30 |
| 68 | LUDOX SM-30 | VI | 0 | 0.15 | 0.4 | 0.6 | 45 |
| 69 | Ultrasil | VII | 0 | 0.3 | 0.4 | 0.75 | 44 |
| 70 | LUDOX SM-30 | VII | 0 | 0.3 | 0.3 | 0.6 | 43 |
| 71 | LUDOX SM-30 | VII | 0 | 0.3 | 0.4 | 0.75 | 51 |
| 72 | LUDOX LS-30 | V | 1 | 0 | 0.15 | 1 | 54 |
| 73 | LUDOX LS-30 | V | 0 | 0.3 | 0.15 | 0.3 | 30 |
| 74 | LUDOX LS-30 | VIII | 0 | 1 | 0.15 | 0.75 | 104 |

The mixtures were stirred until homogenous and then reacted at autogenous pressure in an air oven with tumbling at the temperature and time specified in Table 4. The products were centrifuged, washed three times with deionized water, dried and then subjected to powder X-ray diffraction analysis. The X-ray diffraction patterns showed the product to be MCM-68 zeolite along with the impurity phase designated by the IZA structure code specified in Table 4.

TABLE 4

| Ex. | Temp ° C. | Time days | Impurity Phase (IZA Code) |
|---|---|---|---|
| 21 | 120 | 28 | ERI |
| 22 | 120 | 28 | PAU |
| 23 | 200 | 4 | MFI |
| 24 | 200 | 4 | MFI |
| 25 | 200 | 10 | MFI |
| 26 | 200 | 10 | MFI |
| 27 | 200 | 10 | MFI |
| 28 | 180 | 4 | BEA |
| 29 | 180 | 4 | BEA |
| 30 | 180 | 4 | BEA |
| 31 | 180 | 10 | BEA |
| 32 | 180 | 10 | MTW |
| 33 | 180 | 10 | MTW |
| 34 | 180 | 10 | BEA |
| 35 | 180 | 10 | BEA |
| 36 | 180 | 10 | BEA |
| 37 | 180 | 10 | MTW |
| 38 | 180 | 10 | MTW |
| 39 | 180 | 10 | MTW |
| 40 | 180 | 10 | MTW |
| 41 | 180 | 10 | MFI |
| 42 | 180 | 10 | MTW |
| 43 | 180 | 10 | MTW |
| 44 | 160 | 4 | BEA |
| 45 | 160 | 10 | MTW |
| 46 | 160 | 10 | BEA |
| 47 | 160 | 10 | MTW |
| 48 | 160 | 10 | BEA |
| 49 | 160 | 10 | MTW |
| 50 | 160 | 10 | BEA |
| 51 | 160 | 10 | MTW |
| 52 | 160 | 10 | MTW |
| 53 | 160 | 10 | BEA |
| 54 | 160 | 10 | MTW |
| 55 | 160 | 10 | MTW |
| 56 | 160 | 10 | BEA |
| 57 | 160 | 10 | MTW |
| 58 | 160 | 10 | MTW |
| 59 | 160 | 10 | BEA |
| 60 | 160 | 10 | MTW |
| 61 | 160 | 10 | BEA |
| 62 | 180 | 10 | BEA, MTW |
| 63 | 180 | 10 | BEA, MTW |
| 64 | 180 | 10 | BEA, MTW |
| 65 | 180 | 10 | BEA, MTW |
| 66 | 160 | 10 | BEA, MTW |
| 67 | 160 | 10 | BEA, MTW |
| 68 | 160 | 10 | BEA, MTW |
| 69 | 180 | 10 | MTW |
| 70 | 180 | 10 | MTW |
| 71 | 180 | 10 | MTW |
| 72 | 160 | 7 | Unknown Phase |
| 73 | 160 | 28 | MTW |
| 74 | 200 | 2 | Unknown Phase |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A dication of the structure $R_1$-$R_3$-$R_2$, where $R_1$ is an N-alkylpiperidinium group of the formula

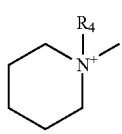

(I)

where $R_2$ is a quinuclidinium group of the formula

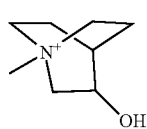
(II)

where $R_3$ is an polymethylene group of the formula $(CH_2)_n$, where n is from 4 to 6, and where $R_4$ is an alkyl group having 1 to 4 carbon atoms.

2. A dication according to claim 1, which is a 3-hydroxy-1-(4-(1-methylpiperidin-1-ium-1-yl)butyl)quinuclidin-1-ium dication of Formula (III) or a 3-hydroxy-1-(5-(1-methylpiperidin-1-ium-1-yl)pentyl)quinuclidin-1-ium dication.

3. A 1,1'-((3as,6as)-octahydropentalene-2,5-diyl)bis(1-methylpiperidin-1-ium)dication.

\* \* \* \* \*